(12) United States Patent
Hiscock et al.

(10) Patent No.: US 7,294,627 B2
(45) Date of Patent: Nov. 13, 2007

(54) CHEMICAL COMPOUNDS

(75) Inventors: Steven Douglas Hiscock, Macclesfield (GB); Stuart Donald Jones, Macclesfield (GB); Daniel Jon Sall, Greenwood, IN (US); Stephen Clinton Young, Stockport (GB); Michael Robert Wiley, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 538 days.

(21) Appl. No.: 10/496,018

(22) PCT Filed: Dec. 9, 2002

(86) PCT No.: PCT/US02/36149

§ 371 (c)(1),
(2), (4) Date: Jun. 1, 2004

(87) PCT Pub. No.: WO03/049737

PCT Pub. Date: Jun. 19, 2003

(65) Prior Publication Data

US 2004/0249151 A1    Dec. 9, 2004

Related U.S. Application Data

(60) Provisional application No. 60/339,324, filed on Dec. 12, 2001.

(51) Int. Cl.
A61K 31/501 (2006.01)
A61K 31/506 (2006.01)
A61K 31/4545 (2006.01)
C07D 401/14 (2006.01)
C07D 401/12 (2006.01)

(52) U.S. Cl. ................. 514/252.03; 514/269; 514/274; 514/318; 544/238; 544/317; 544/328; 544/329; 546/193; 546/194

(58) Field of Classification Search ................ 544/238, 544/317, 328, 329; 546/193, 194; 514/252.03, 514/274, 269, 318
See application file for complete search history.

(56) References Cited

U.S. PATENT DOCUMENTS 6,784,182 B2 * 8/2004 Liebeschuetz et al. . 514/253.09
6,855,715 B1 * 2/2005 Liebeschuetz et al. ... 514/235.2

FOREIGN PATENT DOCUMENTS

| WO | WO 99/11657 | 3/1999 |
| WO | WO 99/11658 | 3/1999 |
| WO | WO 00/76971 | 12/2000 |
| WO | WO 01/96304 | 12/2001 |

OTHER PUBLICATIONS

Jones, Stuart D, et al., Bioorganic & Medicinal Chemistry Letters 11 (2001) 733-736.

* cited by examiner

Primary Examiner—Bernard Dentz
(74) Attorney, Agent, or Firm—Thomas E. Jackson

(57) ABSTRACT

Compounds of formula (I)

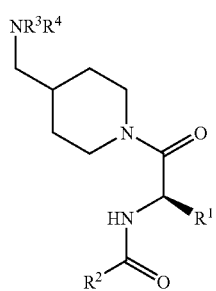

(I)

in which $R^1$, $R^2$, $R^3$ and $R^4$, have the meanings given in the specification are Factor Xa inhibitors useful in the treatment of thrombotic disorders.

14 Claims, No Drawings

CHEMICAL COMPOUNDS

This application claims the benefit of U.S. provisional patent application Ser. No. 60/339,324 filed on Dec. 12, 2001.

The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 99/11657, WO 99/11658 and WO 00/76971 disclose certain compounds containing an aromatic group and a substituted glycine amide residue that bears a cyclic group and a lipophilic group. WO 99/11657, which discloses compounds in which the aromatic group is an amino-substituted isoquinoline group, also generically discloses aminoisoquinoline compounds containing a substituted glycine amide residue that bears an acyclic group.

Surprisingly, compounds containing particular phenyl or indolyl groups and a substituted glycine amide residue bearing a particular 4-N-substituted aminomethylpiperidin-1-yl group have now been found that are selective Factor Xa inhibitors and have particularly advantageous properties.

Accordingly, the present invention provides a compound of formula (I)

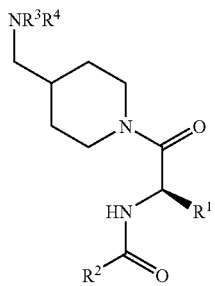

(I)

in which $R^3$ represents pyrid-4-yl which is unsubstituted or bears a substituent at the 2 position selected from trifluoromethyl, cyano and methoxy; pyrimidin-4-yl which is unsubstituted or bears a substituent at the 2 position selected from hydroxy, methoxy, amino, methylamino, trifluoromethyl and cyano; or pyridazin-3-yl;

$R^4$ represents hydrogen or methyl;

$R^1$ represents:

(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy or pyridyl;

(ii) pyridyl, pyrimidyl or pyridazinyl, which is unsubstituted or substituted by a halogen atom;

(iii) furyl, thienyl, imidazolyl, thiazolyl, isothiazolyl, oxazolyl, isoxazolyl, thiadiazolyl, each of which is unsubstituted or substituted by (1-4C)alkyl or amino;

(iv) naphthyl, benzofuryl, benzothienyl, quinolyl or isoquinolyl;

(v) (3-6C)cycloalkyl;

(vi) piperidinyl or tetrahydropyranyl; or (vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and $R^2$ is selected from

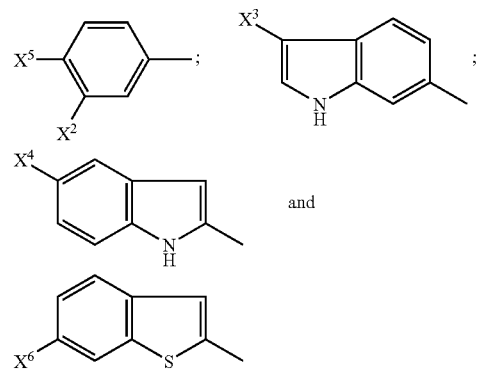

and in which $X^2$ represents a hydrogen atom, a halogen atom or an amino group;

$X^3$ represents a hydrogen atom, a methyl group, a chlorine atom or a bromine atom;

$X^4$ represents a hydrogen atom, a methyl group or a halogen atom;

$X^5$ represents a chlorine atom, a methoxy group or a methyl group; and $X^6$ represents a hydrogen atom, a halogen atom or a methyl group;

or a pharmaceutically acceptable salt thereof.

Compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological and toxicological profiles of activity.

In the compounds according to the invention, unless otherwise indicated, examples of the term "halogen atom" are fluoro and chloro.

In one subgroup of compounds of formula (I), $R^1$ represents (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent), and $R^3$ is as defined hereinabove.

Examples of particular values for $R^3$ in this subgroup are pyrid-4-yl, 2-trifluoromethylpyrid-4-yl, 2-cyanopyrid-4-yl, pyrimidin-4-yl, 2-methoxypyrimidin-4-yl, or pyridazin-3-yl.

In another subgroup of compounds of formula (I), $R^3$ represents pyrid-4-yl which bears a substituent at the 2 position selected from trifluoromethyl, cyano and methoxy; pyrimidin-4-yl which is unsubstituted or bears a substituent at the 2 position selected from hydroxy, methoxy, amino, methylamino, trifluoromethyl and cyano; or pyridazin-3-yl (i.e. not including unsubstituted pyrid-4-yl) and $R^1$ has any of the meanings (i) to (vii) as defined hereinabove.

Examples of particular values for $R^3$ in this subgroup are 2-trifluoromethylpyrid-4-yl, 2-cyanopyrid-4-yl, pyrimidin-4-yl, 2-methoxypyrimidin-4-yl, or pyridazin-3-yl.

Examples of particular values for $R^1$ are:—

(i) phenyl, 2,3-methylenedioxyphenyl, 2-chlorophenyl, 2-methylphenyl, 2-methoxyphenyl, 2-trifluoromethylphenyl, 2-difluoromethoxyphenyl, 4-carboxyphenyl or 4-aminocarbonylphenyl;

(ii) pyrid-2-yl or pyrid-4-yl;

(iii) fur-2-yl, fur-3-yl, thien-2-yl, thien-3-yl, imidazol-2-yl, thiazol-2-yl, thiazol-4-yl, 2-methylthiazol-4-yl or 2-aminothiazol-4-yl;

(iv) naphth-1-yl, naphth-2-yl, benzofuryl, benzothienyl, quinolin-4-yl or quinolin-8-yl;

(v) cyclopropyl, cyclobutyl, cyclopentyl or cyclohexyl;

(vi) piperidin-4-yl or tetrahydropyran-4-yl; or (vii) methyl, ethyl, propyl, 2-propyl, butyl, 2-methylpropyl, hydroxymethyl, 1-hydroxyethyl, methoxymethyl, 1-methoxyethyl, methylthiomethyl, 2-methylthioethyl, prop-2-ylthiomethyl, N,N-dimethylaminomethyl, phenylthiomethyl, pyrid-2-ylthiomethyl, carboxymethyl, 2-carboxyethyl, aminocarbonylmethyl, 2-aminocarbonylethyl, morpholinomethyl, 2,2,2-trifluoroethyl, benzyl, pyrid-2-ylmethyl, pyrid-3-ylmethyl, pyrid-4-ylmethyl, imidazol-1-ylmethyl, imidazol-4-ylmethyl, 3-methylimidazol-4-ylmethyl, cyclohexyl-4-ylmethyl, tetrahydropyran-4-ylmethyl, piperidin-1-ylmethyl or 1-methylpiperidin-4-ylmethyl.

Preferably $R^1$ represents phenyl, 2-chlorophenyl, 2-methoxyphenyl, 2-trifluoromethylphenyl or 2-difluoromethoxyphenyl.

In the groups represented by $R^2$, $X^2$ preferably represents a hydrogen atom or a halogen atom.

More preferably $X^2$ represents a hydrogen atom or a fluorine atom;

$X^3$ represents a hydrogen atom, a chlorine atom or a methyl group;

$X^4$ represents a chlorine atom;

$X^5$ represents a chlorine atom or a methoxy group; and $X^6$ represents a chlorine atom.

Particularly preferred values for $R^2$ are 4-chlorophenyl, 4-methoxyphenyl, indol-6-yl, 3-methylindol-6-yl, 3-chloroindol-6-yl, 5-chloroindol-2-yl or 6-chlorobenzo[b]thiophen-2-yl.

Especial mention may be made of compounds of formula (I) in which $R^2$ is 4-methoxyphenyl, indol-6-yl or 5-chloroindol-2-yl.

It will be appreciated that the compounds of formula (I) contain a center of asymmetry that has the (D) configuration. This is the conformation that would result from construction from a D-α-amino acid $H_2N$—$CH(R^1)COOH$. The compounds may therefore exist and be isolated in a mixture with the corresponding (L) isomer, such as a racemic mixture, or separately. Preferably the compounds are isolated substantially free of the (L) isomer.

It will also be appreciated that the compounds of formula (I) or their pharmaceutically acceptable salts may be isolated in the form of a solvate, and accordingly that any such solvate is included within the scope of the present invention.

The compounds of formula (I) and their pharmaceutically acceptable salts may be prepared by a process, which comprises (a) reacting a compound of formula (II)

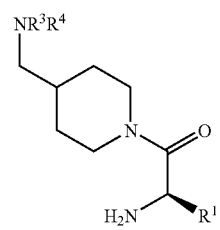

(II)

or a salt thereof, with a compound of formula (III)

(III)

or a reactive derivative thereof;

(b) reacting a compound of formula (IV)

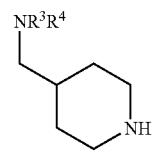

(IV)

or a salt thereof, with a compound of formula (V)

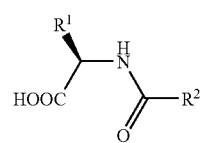

(V)

or a reactive derivative thereof; or (c) deprotecting a compound of formula

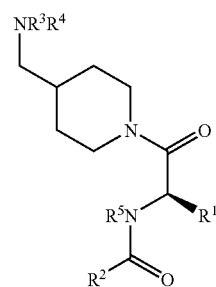

(VI)

in which $R^5$ represents an amino protecting group;

followed, if a pharmaceutically acceptable salt is desired, by forming a pharmaceutically acceptable salt.

The reaction between a compound of formula (II) with a compound of formula (III) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as the chloride in the presence of a base, such as triethylamine.

The reaction between a compound of formula (IV) with a compound of formula (V) may conveniently be performed employing reagents and reaction conditions conventionally used for the formation of an amide bond, for example as described above for the reaction of a compound of formula (II) with a compound of formula (III).

In the compounds of formula (VI), the amino protecting group represented by $R^5$ may be, for example, an arylmethyl group, such as 2,4-dimethoxybenzyl. Such a group may conveniently be removed by treating the compound of formula (VI) with aqueous trifluoroacetic acid. Convenient solvents include dichloromethane.

The compounds of formula (II) may be prepared by reacting a compound of formula (IV) with a compound of formula (VII)

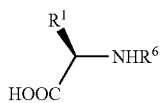

(VII)

in which $R^6$ represents an amino protecting group, such as t-butoxycarbonyl (Boc) to afford a compound of formula (VIII)

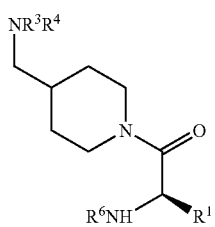

(VIII)

followed by removing the protecting group, for example using trifluoroacetic acid.

The compounds of formula (III) are known.

The compounds of formula (IV) may be prepared by reacting a compound of formula (IX)

(IX)

in which $R^7$ represents a nitrogen protecting group, such as t-butoxycarbonyl, with a compound of formula

(X)

in which $Z^1$ represents a leaving atom or group, such as a halogen atom, in the presence of a base, followed by removing the protecting group $R^7$.

The compounds of formula (V) may be prepared by reacting a compound of formula (XI)

(XI)

in which $R^8$ represents a carboxyl protecting group, for example a (1-6C)alkyl group, such as methyl or ethyl, with a compound of formula (III) to afford a compound of formula (XII)

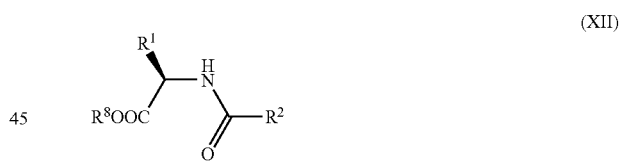

(XII)

followed by removing the protecting group.

The compounds of formula (VI) may be prepared by reacting a compound of formula (XIII)

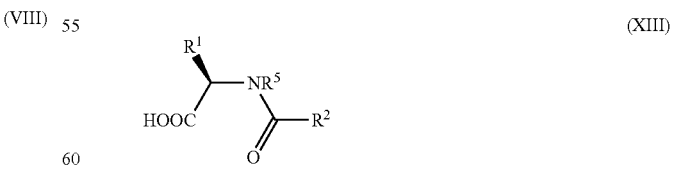

(XIII)

with a compound of formula (IV).

Compounds of formula (XIII) may be prepared using the method described by Ugi et al., Tetrahedron 55 (1999), 7111-7120, for example as depicted in Scheme I below.

Scheme 1

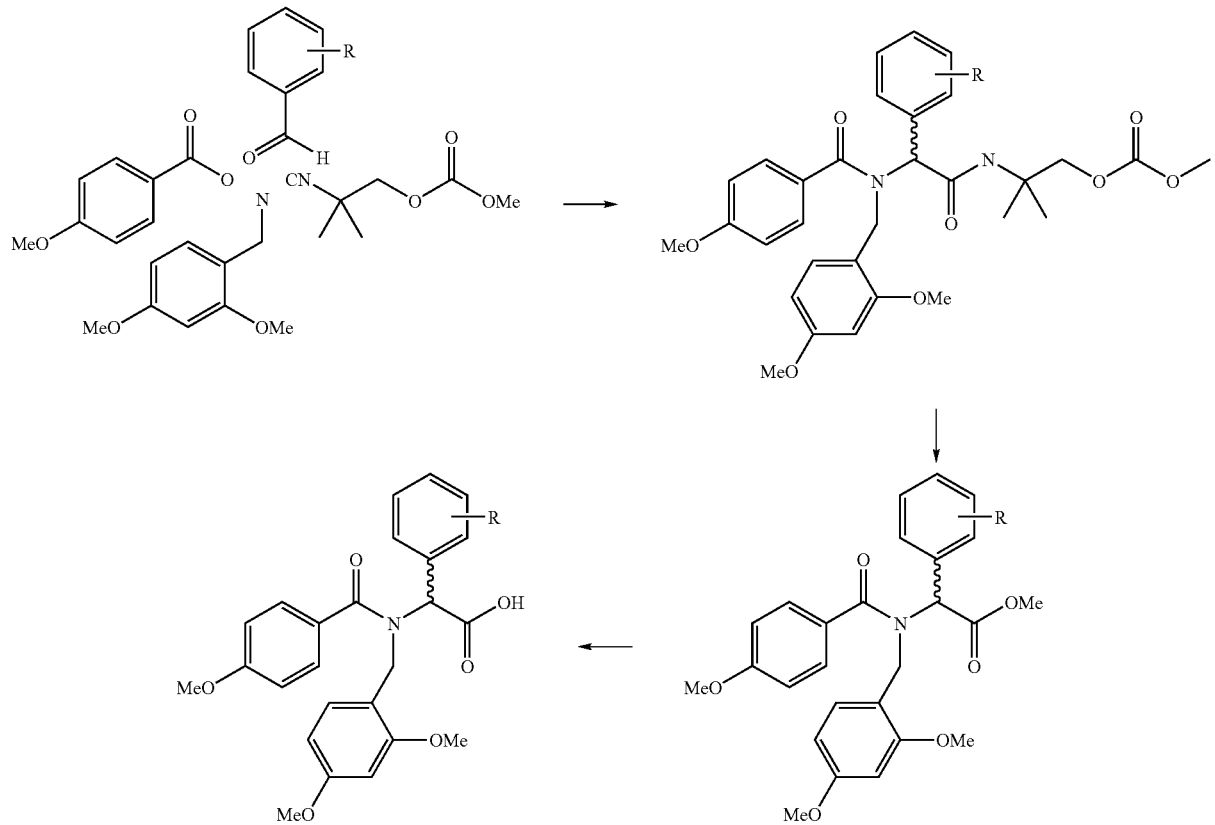

The compounds of formulae (VII) and (XI) are known or may be prepared using conventional methods for the preparation of amino acids protected on the carboxy or amino group, for example by one or more of the following methods:

(i) from aryl or heteroaryl aldehydes via the Strecker synthesis or modifications thereof, via Bucherer-Bergs hydantoin synthesis, or via the Ugi methodology ("Isonitrile Chemistry", Ugi I. Ed.; Academic: New York, 1971; 145-1999, "Multicomponent Reactions with Isocyanides", Domling, A.; Ugi, I. *Angew. Chem. Int. Ed.* 2000, 39, 3168; "Amino Acid Derivatives by Multicomponent Reactions", Dyker, G. *Angew, Chem. Int. Ed. Engl.* 1997, 36, 1700; and also see "A new Class of Convertible Isocyanides in the Ugi Four-Component Reaction", Lindhorst, T.; Bock H.; Ugi, I. *Tetrahedron,* 1999, 55, 7411.) with removal and replacement of protecting groups;

(ii) from styrenes via Sharpless methodology (J. Am. Chem. Soc. 1998, 120, 1207-1217)

(iii) from aryl boronic acids via Petasis methodology (Tetrahedron, 1997, 53, 16463-16470) with removal and replacement of protecting groups;

(iv) from aryl and heteroaryl acetic acids—via Evan's azidation (Synthesis, 1997, 536-540) or by oximation, followed by reduction and addition of protecting groups; or (v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid, or alkylsulphonyl compounds by oxidation of alkylthio compounds;

(vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487-490), or by any other method known in the art or (vii) from oximes of formula

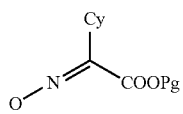

in which Pg is a carboxy protecting group, by reduction.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$-$C_6$ alkyl groups such as methyl, ethyl, t-butyl and t-amyl; aryl($C_1$-$C_4$)alkyl groups such as benzyl, 4-nitro-benzyl, 4-methoxybenzyl, 3,4-dimethoxybenzyl, 2,4-dimethoxy-benzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula RCO in which R represents $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$-$C_4$ alkyl and $C_1$-$C_4$ alkoxy.

Preferred amino protecting groups include benzyloxycarbonyl (CBz) and t-butoxycarbonyl (Boc).

Certain of the intermediates described herein, for example the compounds of formulae (II) and (VI), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Viewed from this aspect the invention provides a pharmaceutical composition, which comprises the compound of formula (I) or a pharmaceutically acceptable salt thereof, together with a pharmaceutically acceptable diluent or carrier.

According to another aspect, the present invention provides the compound of formula (I) or a pharmaceutically acceptable salt thereof, for use in therapy.

According to another aspect, the present invention provides the use of the compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. A particular indication is, for example, prophylaxis of post-operative venous thrombosis following high risk orthopedic surgery (such as hip or knee replacement), primary treatment of venous thrombosis, secondary prevention of ischemic cardiovascular complications following myocardial infarction (in combination with e.g. low dose aspirin), or prevention of embolic stroke in non-valvular atrial fibrillation. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compound of formula (I) will depend upon the nature and severity of the condition being treated, the administration route and the size and species of the subject. In general, quantities in the range of from 0.01 to 100 µM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

Abbreviations used follow IUPAC-IUB nomenclature. Additional abbreviations are LCMS liquid chromatography mass spectrum; 1H NMR signifies that the NMR spectrum was consistent with the assigned structure. RedAl™ refers to sodium bis(2-methoxyethoxy)aluminium hydride. Celite refers to diatomaceous earth. Reagents were obtained from a variety of commercial sources.

Preparation of Intermediates

Substituted N-(4-methoxybenzoyl)-N-(2,4-dimethoxybenzyl)-phenylglycine methyl esters were prepared from the appropriate starting materials using the method described by Ugi et al Tetrahedron 55 (1999) pp 7111-7120.

N-(4-methoxybenzoyl)-N-(2,4-dimethoxybenzyl)-(2-chloro-phenyl)glycine

To a solution of N-(4-methoxybenzoyl)-N-(2,4-dimethoxybenzyl)-(2-chlorophenyl)glycine methyl ester (30 g) in THF (350 ml) is added a solution of lithium hydroxide monohydrate (4.2 g) in water (85 ml) and the mixture is refluxed for 2 h before cooling and evaporation of excess THF in vacuo. The aqueous solution is extracted with ether to remove neutral compounds and the aqueous solution adjusted to pH2 with conc. hydrochloric acid. The acidic solution is extracted with dichloromethane (×3), washed with water, dried (MgSO$_4$) and evaporated in vacuo to give the title compound (27.6 g) as a solid foam.

$^1$Hnmr.

The following compounds were prepared using the method described above:

N-(4-methoxybenzoyl)-N-(2,4-dimethoxybenzyl)-(2-methoxy-phenyl)glycine $^1$Hnmr.

N-(4-methoxybenzoyl)-N-(2,4-dimethoxybenzyl)-(2-difluoromethoxyphenyl)glycine $^1$Hnmr.

1-t-Butoxycarbonyl-4-methylamidopiperidine

To a stirred solution of 1-t-butoxycarbonyl-iso-nipecotic acid (50.0 g, 218 mmol) and triethylamine (29.6 mL, 228 mmol) in tetrahydrofuran (160 mL) at 0° C. is added iso-butylchloroformate dropwise. The mixture is stirred at 0° C. for 30 minutes then diluted with tetrahydrofuran (600 mL) before methylamine is passed through the mixture for 30 minutes. The cooling bath is removed and methylamine is passed through the mixture for 20 minutes. The mixture is stirred at room temperature overnight before excess tetrahydrofuran is removed in vacuo. The residue is taken into water and extracted into ethyl acetate (×3). The combined organic extracts are washed with 1N sodium hydroxide solution, brine, dried (magnesium sulfate), filtered and concentrated in vacuo giving 1-t-butoxycarbonyl-4-methylamidopiperidine (35.6 g, 67%).

LCMS, Luna 30×4.6, file 8, rt, 2.39 min, M+1 243
¹H NMR 1-t-Butoxycarbonyl-4-[(methylamino)methyl]piperidine To a stirred solution of 1-t-butoxycarbonyl-4-methylamidopiperidine (13.0 g, 50.0 mmol) in tetrahydrofuran (160 mL) at 0° C. is added RedAl™ (46.9 mL, 150 mmol) dropwise. Upon complete addition the cooling bath is removed and the mixture is stirred at room temperature for 4.5 hours before, at 0° C., a 50% saturated solution of sodium potassium tartrate is added with caution. The aqueous phase is extracted into ethyl acetate (×3) and the combined organic extracts are washed with brine, dried (magnesium sulfate), filtered and concentrated in vacuo. The residue is emulsified in water, potassium hydrogen sulfate is added until pH 2-3 and the aqueous phase is washed with ethyl acetate (×3). The aqueous phase is made basic by the addition of sodium hydroxide until pH >12 and extracted into ethyl acetate (×3). The combined organic extracts are washed with brine, dried (magnesium sulfate), filtered and concentrated in vacuo giving 1-t-butoxycarbonyl-4-[(methylamino)methyl]piperidine (6.60 g, 60%).

LCMS, Luna 30×4.6, file 8, rt, 1.74 min, M+1 229
¹H NMR 1-t-Butoxycarbonyl-4-{[(2-chloropyrimidin-4-yl)(methyl)amino]methyl}piperidine A stirred suspension of 1-t-butoxycarbonyl-4-[(methylamino)methyl]piperidine (3.50 g, 15.3 mmol), 2,4-dichloropyrimidine (2.74 g, 18.3 mmol) and potassium carbonate (4.15 g, 30.0 mmol) in dimethylformamide (38 mL) is heated at 60° C. for 3 hours. Excess dimethylformamide is removed in vacuo and the residue is taken into water and chloroform. The phases are separated and the aqueous phase is extracted into chloroform (×2). The combined organic extracts are dried (sodium sulfate), filtered and concentrated in vacuo. Flash column chromatography eluting with a gradient of 30% ethyl acetate-hexane to 60% ethyl acetate-hexane provides 1-t-butoxycarbonyl-4-{[(2-chloropyrimidin-4-yl)(methyl)amino]methyl}piperidine (4.23 g, 80%).

LCMS, Luna 30×4.6, file 8, rt, 4.34 min, M+1 341
¹H NMR

4-{[(2-Methoxypyrimidin-4-yl)(methyl)amino]methyl}-piperidine hydrochloride

A stirred suspension of 1-t-butoxycarbonyl-4-{[(2-chloropyrimidin-4-yl)(methyl)amino]methyl}piperidine (1.00 g, 2.93 mmol) and sodium methoxide (633 mg, 11.7 mmol) in methanol (7.3 mL) is heated under reflux for 48 hours. Excess methanol is removed in vacuo and the residue is taken into water and ethyl acetate. The phases are separated and the aqueous phase is extracted into ethyl acetate (×3). The combined organic extracts are dried (sodium sulfate), filtered and concentrated in vacuo. The residue is taken into methanol (100 mL) and hydrogen chloride gas is passed through the solution maintaining <20° C. The mixture is kept at this temperature for 2 hours before it is concentrated in vacuo giving 4-{[(2-methoxypyrimidin-4-yl)(methyl)amino]methyl}piperidine hydrochloride (1.04 g, 100%).

LCMS, M+1 237

1-[t-Butoxycarbonyl-D,L-(2-chlorophenyl)glycinyl]-4-{[(2-methoxypyrimidin-4-yl)(methyl)amino]methyl}piperidine To a stirred suspension of t-butoxycarbonyl-D,L-(2-chlorophenyl)glycine (429 mg, 1.50 mmol), 4-{[(2-methoxypyrimidin-4-yl)(methyl)amino]methyl}piperidine hydrochloride (409 mg, 1.50 mmol), 1-hydroxy-7-azabenzotriazole (225 mg, 1.65 mmol) and triethylamine (0.690 mL, 4.95 mmol) in dimethylformamide (12 mL) at room temperature is added 1-[3-(dimethylamino)propyl]-3-ethylcarbodiimide hydrochloride (316 mg, 1.65 mmol) in a single portion. The mixture is stirred at room temperature for 17 hours before it is concentrated in vacuo. The residue is dissolved in chloroform and saturated sodium bicarbonate and water are added. The phases are separated and the aqueous phase is extracted into chloroform (×2). The combined organic extracts are dried (sodium sulfate), filtered and concentrated in vacuo. Flash column chromatography eluting with a gradient of 100% ethyl acetate to 6% methanol-ethyl acetate provides of 1-[t-butoxycarbonyl-D,L-(2-chlorophenyl)glycinyl]-4-{[(2-methoxypyrimidin-4-yl)(methyl)amino]methyl}piperidine (694 mg, 92%).

LCMS, Luna 30×4.6, file 8, rt, 2.93 min, M+1 504/506

Using a similar procedure and with the appropriate starting materials the following intermediates are also prepared 1-[t-Butoxycarbonyl-D,L-(2-chlorophenyl)glycinyl]-4-{[(methyl)(pyrimidin-4-yl)amino]methyl}piperidine LCMS, Luna 30×4.6, file 8, rt, 2.82 min, M+1 474/476

1-[t-Butoxycarbonyl-D,L-(2-chlorophenyl)glycinyl]-4-{[(methyl)(2-cyanopyridin-4-yl)amino]methyl}piperidine LCMS, Luna 30×4.6, file 8, rt, 4.07 min, M+1 498/500

1-[t-Butoxycarbonyl-D,L-2-(chlorophenyl)glycinyl]-4-{[(methyl)(2-trifluoromethylpyridin-4-yl)amino]methyl}piperidine LCMS, Luna 30×4.6, file 8, rt, 4.18 min, M+1 541/543

1-[t-Butoxycarbonyl-D,L-phenylglycinyl]-4-{[(methyl)(pyridin-4-yl)amino]methyl}piperidine LCMS, Luna 30×4.6, file 8, rt, 2.82 min, M+1 439

1-(t-Butoxycarbonyl-D,L-phenylglycinyl)-4-(pyridin-4-ylamino]methyl}piperidine

LCMS, Luna 30×4.6, file 8, rt, 2.06 min, M+1 425

1-[D,L-(2-Chlorophenyl)glycinyl)-4-{[(2-methoxypyrimidin-4-yl)(methyl)amino]methyl}piperidine To a stirred solution of 1-[t-butoxycarbonyl-D,L-(2-chlorophenyl)glycinyl]-4-{[(2-methoxypyrimidin-4-yl)(methyl)amino]methyl}piperidine (694 mg, 1.38 mmol) and anisole (2.99 mL, 27.5 mmol) in dichloromethane (11 mL) is added trifluoroacetic acid (2.75 mL) maintaining <20° C. The mixture is stirred at room temperature for 4 hours before it is loaded onto an SCX ion exchange column, eluting the basic components with methanol-dichloromethane-triethylamine 50:50:10, concentration in vacuo gives 1-[D,L-(2-chlorophenyl)glycinyl]-4-{[(2-methoxypyrimidin-4-yl)(methyl)amino]methyl}piperidine (520 mg, 93%).

LCMS, M+1 404/406

Using a similar procedure and with the appropriate starting materials the following intermediates are also prepared 1-[D,L-(2-chlorophenyl)glycinyl]-4-{[(methyl)(pyrimidin-4-yl)amino]methyl}piperidine

LCMS, M+1 374/376

1-[D,L-(2-chlorophenyl)glycinyl]-4-{[(methyl)(2-cyanopyridin-4-yl)amino]methyl}piperidine

LCMS, M+1 398/400

1-[D,L-(2-chlorophenyl)glycinyl]-4-{[(methyl)(2-trifluoromethylpyridin-4-yl)amino]methyl}piperidine

LCMS, M+1 441/443

1-(D,L-phenylglycinyl)-4-[(methyl)(pyridin-4-yl)amino]methyl}piperidine

LCMS, M+1 339

1-[D,L-phenylglycinyl]-4-(pyridin-4-ylaminomethyl)piperidine

LCMS, M+1 325

EXAMPLE 1

1-[4-Methoxybenzoyl-D,L-(2-chlorophenyl)glycinyl]-4-{[(2-methoxypyrimidin-4-yl)(methyl)amino]methyl}piperidine To a stirred suspension of anisic acid (196 mg, 1.29 mmol), 1-[D,L-(2-chlorophenyl)glycinyl]-4-{[(2-methoxypyrimidin-4-yl)(methyl)amino]methyl}piperidine (520 mg, 1.29 mmol) and 1-hydroxy-7-azabenzotriazole (193 mg, 1.42 mmol) in dimethylformamide (10.5 mL) at room temperature is added 1-[3-(dimethylamino)propyl]-3-ethylcarbodiimide hydrochloride (271 mg, 1.42 mmol) in a single portion. The mixture is stirred at room temperature for 17 hours before it is concentrated in vacuo. The residue is dissolved in chloroform and saturated sodium bicarbonate and water are added. The phases are separated and the aqueous phase is extracted into chloroform (×2). The combined organic extracts are dried (sodium sulfate), filtered and concentrated in vacuo. Preparative hplc (water-acetonitrile-trifluoroacetic acid) followed by formation of the free base (chloroform-saturated sodium bicarbonate) and subsequent trituration provides 1-[4-methoxybenzoyl-D,L-(2-chlorophenyl)glycinyl]-4-{[(2-methoxypyrimidin-4-yl)(methyl)amino]methyl}piperidine.

LCMS, Luna 30×4.6, file 8, rt, 3.04 min, M+1 538/540
$^1$H NMR

Using a similar procedure and with the appropriate starting materials the following compounds are also prepared

EXAMPLE 2

1-[4-Methoxybenzoyl-D,L-(2-chlorophenyl)glycinyl]-4-{[(methyl)(pyrimidin-4-yl)amino]methyl}piperidine LCMS, Luna 30×4.6, file 8, rt, 2.82 min, M+1 508/510
$^1$H NMR

EXAMPLE 3

1-[4-Methoxybenzoyl-D,L-(2-chlorophenyl)glycinyl]-4-{[(methyl)(2-cyanopyridin-4-yl)amino]methyl}piperidine LCMS, Luna 30×4.6, file 8, rt, 3.74 min, M+1 532/534
$^1$H NMR

EXAMPLE 4

1-[4-Methoxybenzoyl-D,L-(2-chlorophenyl)glycinyl]-4-{([(methyl)(2-trifluoromethylpyridin-4-yl)amino]methyl}-piperidine LCMS, Luna 30×4.6, file 8, rt, 3.91 min, M+1 475/477
$^1$H NMR

EXAMPLE 5

1-(Indole-6-carbonyl-D,L-phenylglycinyl)-4-{[(methyl)(pyridin-4-yl)amino]methyl}piperidine LCMS, Luna 30×4.6, file 8, rt, 2.66 min, M+1 482
$^1$H NMR

EXAMPLE 6 (DELETED)

Preparation of Intermediates

4-{[(Pyrimidin-4-yl)(methyl)amino]methyl}piperidine hydrochloride

A suspension of 1-t-butoxycarbonyl-4-{[(2-chloropyrimidin-4-yl)(methyl)amino]methyl}piperidine (3.00 g, 8.80 mmol) and 5% palladium on activated carbon (1.87 g, 0.880 mmol) in ethanol (70 mL) and 1N sodium acetate solution (17.6 mL) is stirred rapidly under 1 atmosphere of hydrogen for 2 hours. After the atmosphere of hydrogen is replaced with argon the mixture is filtered through a bed of Celite™ and ethyl acetate, water and saturated sodium bicarbonate are added to the solution. The phases are separated and the aqueous phase is extracted into ethyl acetate (×3). The combined organic extracts are dried (sodium sulfate), filtered and concentrated in vacuo. The residue is taken into methanol (270 mL) and hydrogen chloride gas is passed through the solution maintaining <20° C. The mixture is kept at this temperature for 2 hours before it is concentrated in vacuo and freeze-dried from water providing 4-{[(pyrimidin-4-yl)(methyl)amino]methyl}piperidine hydrochloride (2.63 g, 100%).

LCMS, M+1 207

4-{[(Methyl)(2-cyanopyridin-4-yl)amino]methyl}piperidine hydrochloride

A stirred suspension of 1-t-butoxycarbonyl-4-[(methylamino)methyl]piperidine (3.50 g, 15.3 mmol), 2-cyano-4- chloropyridine (2.54 g, 18.3 mmol) and potassium carbonate (4.15 g, 30.0 mmol) in dimethylformamide (38 mL) is heated at 95° C. for 17 hours. Excess dimethylformamide is removed in vacuo and the residue is taken into water and chloroform. The phases are separated and the aqueous phase is extracted into chloroform (×2). The combined organic extracts are washed with 2.5% hydrogen chloride solution, extracted into chloroform (×4) and the combined organic extracts are dried (sodium sulfate), filtered and concentrated in vacuo. The residue is taken into methanol (500 mL) and hydrogen chloride gas is passed through the solution maintaining <20° C. The mixture is kept at this temperature for 3 hours before it is concentrated in vacuo. The residue is taken into water and washed with ethyl acetate (×2). The aqueous phase is made basic by the addition of sodium hydroxide until pH >12 and extracted into ethyl acetate (×8). The combined organic extracts are dried (sodium sulfate), filtered and concentrated in vacuo. The free base is taken into 2.5% hydrogen chloride solution and freeze-dried providing 4-{[(methyl)(2-cyanopyridin-4-yl)amino]methyl}piperidine hydrochloride (3.25 g, 72%).

LCMS, M+1 231

1-t-Butoxycarbonyl-4-{[(methyl)(2-trifluoromethylpyridin-4-yl)amino]methyl}piperidine A stirred solution of 2-trifluoromethylpyridin-4-ol (12.5 g, 76.6 mmol) and dimethylformamide (3.00 mL) in phosphorus oxychloride (75 mL) is heated under reflux for 2 hours before excess phosphorus oxychloride is removed in vacuo. The residue is poured onto an ice-water mixture and extracted into ethyl acetate (×5). The combined organic extracts dried (sodium sulfate), filtered and concentrated in vacuo. The non-basic components of the mixture are eluted through a SCX column washing with a 1:1 mixture of methanol-dichloromethane. A stirred suspension of the residue, 1-t-butoxycarbonyl-4-[(methylamino)methyl]piperidine (1.11 g, 4.85 mmol) and potassium carbonate (4.15 g, 30.0 mmol) in dimethylformamide (38 mL) is heated at 90° C. for 13 hours. Excess dimethylformamide is removed in vacuo, the residue is taken into chloroform and washed with 2.5% hydrogen chloride solution. The aqueous layer is extracted into chloroform (×3) and the combined organic extracts are dried (sodium sulfate), filtered and concentrated in vacuo. Flash column chromatography eluting with a gradient of 30% ethyl acetate-hexane to 50% ethyl acetate-hexane provides 1-t-butoxycarbonyl-4-{[(methyl)(2-trifluoromethylpyridin-4-yl)amino]methyl}piperidine (520 mg, 2%).

MS, Luna 30×4.6, file 8, rt, 3.91 min, M+1 374

$^1$H NMR

4-{[(Methyl)(2-trifluoromethylpyridin-4-yl)amino]methyl}-piperidine hydrochloride Hydrogen chloride gas is passed through a methanol (500 mL) solution of 1-t-butoxycarbonyl-4-{[(methyl)(2-trifluoromethylpyridin-4-yl)amino]methyl}piperidine maintaining <20° C., for 5 minutes. The mixture is kept at this temperature for 1 hour before it is concentrated in vacuo providing 4-{[(methyl)(2-trifluoromethylpyridin-4-yl)amino]methyl}piperidine hydrochloride (430 mg, 100%).

LCMS, M+1 274

1-t-Butoxycarbonyl-4-(2,3,5,6-tetrachloropyridin-4-ylaminomethyl)piperidine

A stirred suspension of 1-t-butoxycarbonyl-4-(aminomethyl)piperidine (16.1 g, 75.0 mmol), pentachloropyridine (20.7 g, 82.5 mmol) and potassium carbonate (20.7 g, 150 mmol) in dimethylformamide (180 mL) is heated at 60° C. for 2 hours. Excess dimethylformamide is removed in vacuo and the residue is taken into water and chloroform. The phases are separated and the aqueous phase is extracted into chloroform (×2). The combined organic extracts are dried (sodium sulfate), filtered and concentrated in vacuo. Filtration through a silica plug eluting with a gradient of 30% diethyl ether-hexane then 60% diethyl ether-hexane provides 1-t-butoxycarbonyl-4-(2,3,5,6-tetrachloropyridin-4-ylaminomethyl)piperidine (18.5 g, 57%).

LCMS, Luna 30×4.6, file 8, rt, 5.86 min, M+1 428/430/432/434

$^1$H NMR 4-(Pyridin-4-ylaminomethyl)piperidine hydrochloride

A suspension of 1-t-butoxycarbonyl-4-(2,3,5,6-tetrachloropyridin-4-ylaminomethyl)piperidine (18.5 g, 43.1 mmol), sodium acetate (21.2 g, 259 mmol) and 5% palladium on activated carbon (9.17 g, 4.31 mmol) in ethanol (340 mL)/methanol (170 mL) is stirred rapidly under 1 atmosphere of hydrogen for 20 hours. After the atmosphere of hydrogen is replaced with argon the mixture is filtered through a bed of Celite™ washing with methanol. The mixture is concentrated in vacuo and the residue is taken into chloroform and saturated sodium bicarbonate solution. The phases are separated and the aqueous phase is extracted into chloroform (×2). The combined organic extracts are dried (sodium sulfate), filtered and concentrated in vacuo. The residue is taken into methanol (1.20 L) and hydrogen chloride gas is passed through the solution maintaining <20° C. The mixture is kept at this temperature for 7 hours before it is concentrated in vacuo giving 4-(pyridin-4-ylaminomethyl)piperidine hydrochloride.

LCMS, M+1 192

1-t-Butoxycarbonyl-4-{[(methyl)(pyridin-4-yl)amino]methyl}-piperidine

A suspension of 1-t-butoxycarbonyl-4-[(methylamino)methyl]piperidine (4.28 g, 18.8 mmol), 4-bromopyridine hydrochloride (4.82 g, 22.5 mmol) in 1,4-dioxane (60 mL) is degassed by sonication and passing argon through the mixture for 15 minutes. Sodium t-butoxide (5.77 g, 60.0 mmol), tris(dibenzylideneacetone) dipalladium (858 mg, 0.938 mmol) and tri-t-butyl phosphine (0.5M in toluene; 3 mL, 1.50 mmol) are added sequentially. The system is sealed, evacuated and back-filled with argon (×5), then heated at 60° C. for 48 hours. The mixture is poured onto a 1:1 mixture of water-ethyl acetate (4 mL), Celite™ is added and the mixture is filtered through a bed of Celite™. The phases are separated and the aqueous phase is extracted into ethyl acetate (×3). The combined organic extracts are washed with brine, dried (sodium sulfate), filtered and concentrated in vacuo. The residue is emulsified in water, potassium hydrogen sulfate is added until pH 2-3 and the aqueous phase is washed with ethyl acetate (×3). The aqueous phase is made basic by the addition of sodium hydroxide until pH >12 and extracted into ethyl acetate (×4). The combined organic extracts are washed with brine, dried (magnesium sulfate), filtered and concentrated in vacuo giving 1-t-butoxycarbonyl-4-{[(methyl)(pyridin-4-yl) amino]methyl}piperidine (5.23 g, 91%).

LCMS, Luna 30×4.6, file 8, rt, 2.17 min, M+1 306
$^1$H NMR

4-{[(Methyl)(pyridin-4-yl)amino]methyl}piperidine hydrochloride

Hydrogen chloride gas is passed through a methanol (500 mL) solution of 1-t-butoxycarbonyl-4-{[(methyl)(pyridin-4-yl)amino]methyl}piperidine maintaining <20° C., for 5 minutes. The mixture is kept at this temperature for 7 hours, then at 4° C. for 16 hours before it is concentrated in vacuo providing 4-{[(methyl)(pyridin-4-yl)amino]methyl}piperidine hydrochloride (4.85 g, >100%).

LCMS, M+1 206

EXAMPLE 7

1-[4-Methoxybenzoyl-D,L-(2-chlorophenyl)glycinyl]-4-{[(methyl)(pyridin-4-ylamino]methyl}piperidine hydrochloride To a stirred suspension of N-(2,4-dimethoxybenzyl)-N-(4-methoxybenzoyl)-D,L-(2-chlorophenyl)glycine (500 mg, 1.06 mmol), 4-{[(methyl)(pyridin-4-yl)amino]methyl}piperidine hydrochloride (296 mg, 1.06 mmol) and triethylamine (0.593 mL, 4.26 mmol) in dimethylformamide (8 mL) at room temperature is added 2-(1H-benzotriazol-1-yl)-1,1,3,3-tetramethyluronium tetrafluoroborate (359 mg, 1.12 mmol) in a single portion. The mixture is stirred at room temperature for 3 hours before it is concentrated in vacuo. The residue is dissolved in chloroform, saturated sodium bicarbonate and water are added and the mixture is filtered through a bed of Celite™. The phases are separated and the aqueous phase is extracted into chloroform (×2). The combined organic extracts are dried (sodium sulfate), filtered and concentrated in vacuo. To a stirred solution of the residue in dichloromethane (11 mL)—water (0.20 mL) is added trifluoroacetic acid (2.00 mL) maintaining <20° C. The mixture is stirred at room temperature for 45 minutes before it is concentrated in vacuo and the residue washed with hexane (×2) and diethyl ether (×2). Preparative hplc (water-acetonitrile-trifluoroacetic acid) followed by formation of the free base (chloroform-saturated sodium bicarbonate). The free base is taken into dichloromethane and hydrogen chloride (1M solution in diethyl ether) is added, concentration in vacuo and freeze-drying from water provides 1-[4-methoxybenzoyl-D,L-(2-chlorophenyl)glycinyl]-4-{[(methyl)(pyridin-4-ylamino)]methyl}piperidine hydrochloride (248 mg, 43%).

LCMS, Luna 30×4.6, file 8, rt, 2.71 min, M+1 507/509
$^1$H NMR

Using a similar procedure and with the appropriate starting materials the following compounds are also prepared

EXAMPLE 8

1-[4-Methoxybenzoyl-D,L-(2-methoxyphenyl)glycinyl)]-4-{[(methyl)(pyridin-4-ylamino)]methyl}piperidine LCMS, Luna 30×4.6, file 8, rt, 2.66 min, M+1 503
$^1$H NMR

EXAMPLE 9

1-[4-Methoxybenzoyl-D,L-(2-difluoromethoxyphenyl)glycinyl]-4-{[(methyl)(pyridin-4-ylamino] methyl}piperidine LCMS, Luna 30×4.6, file 8, rt, 2.82 min, M+1 539
$^1$H NMR Preparation of Intermediates

1-t-Butoxycarbonyl-4-{[(2-chloropyrimidin-4-yl) amino]methyl)}piperidine

A stirred suspension of 1-t-butoxycarbonyl-4-aminomethyl)piperidine (7.50 g, 35.0 mmol), 2,4-dichloropyrimidine (5.47 g, 36.7 mmol) and potassium carbonate (9.67 g, 70.0 mmol) in dimethylformamide (84 mL) is stirred at room temperature for 2 hours. Excess dimethylformamide is removed in vacuo and the residue is taken into water and chloroform. The phases are separated and the aqueous phase is extracted into chloroform (×2). The combined organic extracts are dried (sodium sulfate), filtered and concentrated in vacuo. Flash column chromatography eluting with a gradient of 50% ethyl acetate-hexane to 80% ethyl acetate-hexane provides 1-t-butoxycarbonyl-4-[(2-chloropyrimidin-4-ylamino)methyl]piperidine (7.89 g, 69%).

LCMS, Luna 30×4.6, file 8, rt, 4.12 min, M+1 327/329
$^1$H NMR

Using a similar procedure and with the appropriate starting materials the following intermediates are also prepared.

1-t-Butoxycarbonyl-4-{[(6-chloropyridazin-3-yl) amino]-methylpiperidine

From 1-t-butoxycarbonyl-4-(aminomethyl)piperidine and 3,6-dichloropyridazine.

LCMS, Luna 30×4.6, file 8, rt, 4.45 min, M+1 327/329
$^1$H NMR

1-t-Butoxycarbonyl-4-{[(6-chloropyridazin-3-yl) (methyl)-amino]methyl}piperidine From 1-t-butoxycarbonyl-4-[(methylamino)methyl]piperidine and 3,6-dichloropyridazine.

LCMS, Luna 30×4.6, file 8, rt, 4.18 min, M+1 341/343
$^1$H NMR

4-[(Pyrimidin-4-ylamino)methyl]piperidine hydrochloride

A suspension of 1-t-butoxycarbonyl-4-[(2-chloropyrimidin-4-ylamino)methyl]piperidine (8.40 g, 25.7 mmol), sodium acetate (4.22 g, 51.4 mmol) and 5% palladium on activated carbon (5.47 g, 2.57 mmol) in ethanol (205 mL) and water (51 mL) is stirred rapidly under 1 atmosphere of hydrogen for 24 hours. After the atmosphere of hydrogen is replaced with argon the mixture is filtered through a bed of Celite™ and the mixture is concentrated in vacuo. Chloroform, water and saturated sodium bicarbonate are added, the phases are separated and the aqueous phase is extracted into chloroform (×3). The combined organic extracts are dried (sodium sulfate), filtered and concentrated in vacuo. The residue is taken into methanol (750 mL) and hydrogen chloride gas is passed through the solution maintaining the temperature at less than 20° C. The mixture is kept at this temperature for 24 hours before it is concentrated in vacuo and freeze-dried from water, providing 4-[(pyrimidin-4-ylamino)methyl]piperidine hydrochloride (5.82 g, 99%).
LCMS, M+1 193

Using a similar procedure and with the appropriate starting materials the following intermediates are also prepared.

4-[(Pyridazin-3-ylamino)methyl]piperidine hydrochloride

From 1-t-butoxycarbonyl-4-[(6-chloropyridazin-3-ylamino)methyl]piperidine
LCMS, M+1 193

4-{[(Pyridazin-3-yl)(methyl)amino]methyl}piperidine hydrochloride

From 1-t-butoxycarbonyl-4-{[(6-chloropyridazin-3-yl)(methyl)amino]methyl}piperidine
LCMS M+1 207

Using a coupling procedure as described above for the preparation of 1-[t-butoxycarbonyl-D,L-(2-chlorophenyl)glycinyl]-4-{[2-methoxypyrimidin-4-yl)(methyl)amino]methyl}piperidine with the appropriate starting materials the following intermediates are prepared.

1-[t-Butoxycarbonyl-D,L-(2-chlorophenyl)glycinyl]-4-[(pyrimidin-4-ylamino)methyl]piperidine From 1-t-butoxycarbonyl-D,L-(2-chlorophenyl)glycine and 4-[(pyrimidin-4-ylamino)methyl]piperidine hydrochloride.
LCMS, Luna 30×4.6, file 8, rt, 3.31 min, M+1 460/462

1-[t-Butoxycarbonyl-D,L-(2-chlorophenyl)glycinyl]-4-[(pyridazin-3-ylamino)methyl]piperidine From 1-t-butoxycarbonyl-D,L-(2-chlorophenyl)glycine and 4-[(pyridazin-3-ylamino)methyl]piperidine hydrochloride
LCMS, Luna 30×4.6, file 8, rt, 3.47 min, M+1 460/462

1-[t-Butoxycarbonyl-D,L-(2-chlorophenyl)glycinyl]-4-{[(pyridazin-3-yl)(methyl)amino]methyl}piperidine From 1-t-butoxycarbonyl-D,L-(2-chlorophenyl)glycine and 4-{[(pyridazin-3-yl)(methyl)amino]methyl}piperidine hydrochloride
LCMS, Luna 30×4.6, file 8, rt, 3.26 min, M+1 474/476

1-[t-Butoxycarbonyl-D,L-(2-trifluoromethylphenyl)glycinyl]-4-[(pyridin-4-ylamino)methyl]piperidine From 1-t-butoxycarbonyl-D,L-(2-trifluoromethylphenyl)glycine and 4-[(pyridin-4-ylamino)methyl]piperidine
LCMS, Luna 30×4.6, file 8, rt, 2.98 min, M+1 493

1-[t-Butoxycarbonyl-D,L-(2-trifluoromethylphenyl)glycinyl]-4-{[(pyridin-4-yl)(methyl)amino]methyl}piperidine From 1-t-butoxycarbonyl-D,L-(2-trifluoromethylphenyl)glycine and 4-{[(pyridin-4-yl)(methyl)amino]methyl}piperidine
LCMS, Luna 30×4.6, file 8, rt, 3.04 min, M+1 507

1-[t-Butoxycarbonyl-D,L-(2-chlorophenyl)glycinyl]-4-[(pyridin-4-ylamino)methyl]piperidine From 1-t-butoxycarbonyl-D,L-(2-chlorophenyl)glycine and 4-[(pyridin-4-ylamino)methyl]piperidine
LCMS, Luna 30×4.6, file 8, rt, 2.93 min, M+1 459/461

Using a similar deprotection procedure as described above for the preparation of 1-[D,L-(2-chlorophenyl)glycinyl]-4-{[(2-methoxypyrimidin-4-yl)(methyl)amino]methyl}piperidine with the appropriate starting materials the following intermediates are also prepared.

1-[D,L-(2-chlorophenyl)glycinyl]-4-[(pyrimidin-4-ylamino)methyl]piperidine

From 1-t-butoxycarbonyl-[D,L-(2-chlorophenyl)glycinyl]-4-[(pyrimidin-4-ylamino)methyl]piperidine
LCMS, M+1 360/362

1-[D,L-(2-chlorophenyl)glycinyl]-4-[(pyridazin-3-ylamino)methyl]piperidine

From 1-t-butoxycarbonyl-[D,L-(2-chlorophenyl)glycinyl]-4-[(pyridazin-3-ylamino)methyl]piperidine
LCMS, M+1 360/362

1-[D,L-(2-chlorophenyl)glycinyl]-4-{[(pyridazin-3-yl)(methyl)amino]methyl}piperidine From 1-t-butoxycarbonyl-[D,L-(2-chlorophenyl)glycinyl]-4-{[(pyridazin-3-yl)(methyl)amino]methyl}piperidine
LCMS, M+1 374/376

1-[D,L-(2-trifluoromethylphenyl)glycinyl]-4-[(pyridin-4-ylamino)methyl]piperidine From 1-t-butoxycarbonyl-[D,L-(2-trifluoromethylphenyl)-glycinyl]-4-[(pyridin-4-ylamino)methyl]piperidine
LCMS, M+1 393

1-[D,L-(2-trifluoromethylphenyl)glycinyl]-4-{[(pyridin-4-yl)(methyl)amino]methyl}piperidine From 1-t-butoxycarbonyl-[D,L-(2-trifluoromethylphenyl)-glycinyl]-4-{[(pyridin-4-yl)(methyl)amino]methyl}piperidine
LCMS, M+1 407

1-[D,L-(2-chlorophenyl)glycinyl]-4-[(pyridin-4-ylamino)methyl]piperidine

From 1-t-butoxycarbonyl-[D,L-(2-chlorophenyl)glycinyl]-4-[(pyridin-4-ylamino)methyl]piperidine
LCMS, 359/361

Using a similar coupling procedure as described above for the preparation of 1-[4-methoxybenzoyl-D,L-(2-chlorophenyl)glycinyl]-4-{[(2-methoxypyrimidin-4-yl)(methyl)amino]methyl}piperidine and with the appropriate starting materials the following compounds are also prepared.

EXAMPLE 10

1-[4-Methoxybenzoyl-D,L-(2-chlorophenyl)glycinyl]-4-[(pyrimidin-4-yl)methylamino]piperidine From anisic acid and 1-[D,L-(2-chlorophenyl)glycinyl)-4-[(pyrimidin-4-ylamino)methyl]piperidine LCMS, Luna 30×4.6, file 8, rt, 3.31 min, M+1 494/496
¹H NMR

EXAMPLE 11

1-[4-Methoxybenzoyl-D,L-(2-chlorophenyl)glycinyl)-4-[(pyridazin-3-ylamino)methyl]piperidine From anisic acid and 1-[D,L-(2-chlorophenyl)glycinyl]-4-[(pyridazin-3-ylamino)methyl]piperidine
LCMS, Luna 30×4.6, file 8, rt, 3.36 min, M+1 494/496
¹H NMR

EXAMPLE 12

1-[4-Methoxybenzoyl-D,L-(2-chlorophenyl)glycinyl]-4-{[(pyridazin-3-yl)methylamino]methyl}piperidine From anisic acid and 1-[D,L-(2-chlorophenyl)glycinyl]-4-{[(pyridazin-3-yl)methylamino]methyl}piperidine
LCMS, Luna 30×4.6, file 8, rt, 3.42 min, M+1 508
¹H NMR

EXAMPLE 13

1-[4-Methoxybenzoyl-D,L-(2-trifluoromethylphenyl)glycinyl]-4-[(pyridin-4-ylamino)methyl]piperidine hydrochloride To a stirred suspension of anisic acid (532 mg, 3.50 mmol), 1-[D,L-(2-trifluoromethylphenyl)glycinyl]-4-[(pyridin-4-ylamino)methyl]piperidine (1.37 g, 3.50 mmol) and 1-hydroxy-7-azabenzotriazole (525 mg, 3.85 mmol) in dimethylformamide (28 mL) at room temperature is added 1-[3-(dimethylamino)propyl]-3-ethylcarbodiimide hydrochloride (738 mg, 3.85 mmol) in a single portion. The mixture is stirred at room temperature for 17 hours before it is concentrated in vacuo. The residue is dissolved in chloroform and saturated sodium bicarbonate and water are added. The phases are separated and the aqueous phase is extracted into chloroform (×2). The combined organic extracts are dried (sodium sulfate), filtered and concentrated in vacuo. Preparative hplc (water-acetonitrile-trifluoroacetic acid) is followed by formation of the free base (chloroform-saturated sodium bicarbonate). Treatment of the free-base in dichloromethane solution with 1 equivalent of HCl in diethyl ether and subsequent freeze-drying from water provides 1-[4-methoxybenzoyl-D,L-(2-trifluoromethylphenyl)glycinyl]-4-[(pyridin-4-ylamino)methyl]piperidine hydrochloride (861 mg, 44%).
LCMS, Luna 30×4.6, file 8, rt, 3.53 min, M+1 527
¹H NMR Using a similar procedure and with the appropriate starting materials the following compounds are also prepared.

EXAMPLE 14

1-[4-Methoxybenzoyl-D,L-(2-trifluoromethylphenyl)glycinyl]-4-{[(pyridin-4-yl)(methyl)amino]methyl}piperidine hydrochloride From anisic acid and 1-[D,L-(2-trifluoromethylphenyl)-glycinyl]-4-{[(pyridin-4-ylamino)]methyl}piperidine
LCMS, Luna 30×4.6, file 8, rt, 3.26 min, M+1 541
¹H NMR

EXAMPLE 15

1-[4-Methoxybenzoyl-D,L-(2-chlorophenyl)glycinyl]-4-[(pyridin-4-ylamino)methyl]piperidine hydrochloride From anisic acid and 1-[D,L-(2-chlorophenyl)glycinyl]-4-[(pyridin-4-ylamino)methyl]piperidine
LCMS, Luna 30×4.6, file 8, rt, 3.31 min, M+1 494/496
¹H NMR Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 μL buffer (0.06 M tris, 0.3 M NaCl, pH 7.4); 25 μL inhibitor test solution (in MeOH); 25 μL human factor Xa (32 nM in 0.03 M tris, 0.15 M NaCl, 1 mg/mL HSA); finally, 150 μL BzIleGluGlyArgpNA (0.3 mM in water) added within 2 min to start hydrolysis. Final [factor Xa] is 3.2 nM. [Free Xa] and [bound Xa] are determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent $Kass=[E:I]/[E_f][I_f]=[E_b]/[E_f][I^o-I^b]$. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347+/−0.031 mM [n=4]; and Vmax was 13.11+/−0.76 μM/min.

Kass values are determined with thrombin and other proteases using the same protocol with the following enzyme and substrate concentrations:

thrombin, 5.9 nM with 0.2 mM BzPheValArgpNA;

factor XIa, 1.2 nM with 0.4 mM pyroGluProArgpNA;

factor XIIa, 10 nM with 0.2 mM HDProPheArgpNA;

plasmin, 3.4 nM with 0.5 mM HDValLeuLyspNA;

nt-PA, 1.2 nM with 0.8 mM HDIleProArgpNA;

urokinase, 0.4 nM with 0.4 mM pyroGluGlyArgpNA;

aPC, 3 nM with 0.174 mM pyroGluProArgpNA;

plasma kallikrein, 1.9 nM with D-ProPheArgpNA; and bovine trypsin, 1.4 nM with 0.18 mM BzPheValArgpNA.

CITATIONS (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489-3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173-183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265-300.

(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649-663 (2000).

The compounds of formula (I) exemplified herein have been found to exhibit a Kass of greater than $1 \times 10^6$ L/mole in the enzyme inhibition assay. For example, the compounds of Examples 6 and 7 have been found to exhibit Kass values of about 165 and $122 \times 10^6$ L/mole, respectively.

The ability of a test compound to elongate Partial Thromboplastin Time (Prothrombin Time) may be evaluated in the following test protocols.

Partial Thromboplastin Time (Prothrombin) Test Protocol

Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 µL of plasma are pipetted into in a glass test tube, 1 µL of test compound in DMSO is added, and allowed to warm to 37° over two minutes. 100 µL of warm (37°) Manchester (tissue thromboplastin) reagent (Helena Biosciences, UK) is added, allowed to equilibrate for two minutes. 100 µL of warm (37°) 25 mM calcium chloride solution is added to initiate clotting. The test tube is tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention have been found to significantly elongate the partial thromboplastin time (Prothrombin time).

Alternative Prothrombin Time and APTT Protocols

Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT Assay

75 µL plasma Citrol Baxter-Dade Citrated Normal Human Plasma

25 µL test solution

75 µL Actin Baxter-Dade Activated Cephaloplastin incubate 2 min min. @ 37° C.

75 µl $CaCl_2$ (0.02 M)

PT Assay

75 µL plasma

25 µL test solution

75 µL saline incubate 1 min. @ 37° C.

75 µL Innovin Baxter-Dade Recombinant Human Tissue Factor

The invention claimed is:

1. A compound of formula (I)

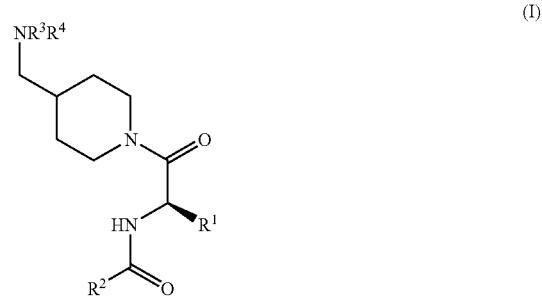

in which

R³ represents pyrid-4-yl which bears a substituent at the 2 position selected from trifluoromethyl, cyano and methoxy; pyrimidin-4-yl which is unsubstituted or bears a substituent at the 2 position selected from hydroxy, methoxy, amino, methylamino, trifluoromethyl and cyano; or pyridazin-3-yl;

R⁴ represents hydrogen or methyl;

R¹ represents:

(i) phenyl which is unsubstituted or substituted by methylenedioxy or by a substituent selected from halogen, (1-4C)alkyl, hydroxy, (1-4C)alkoxy, trifluoromethyl, difluoromethoxy, trifluoromethoxy, (1-4C)alkylthio, (1-4C)alkylsulfinyl, (1-4C)alkylsulfonyl, carboxy, aminocarbonyl, amino, (2-4C)alkanoylamino, aminosulfonyl, (1-4C)alkylaminosulfonyl, nitro, phenyl, phenoxy, benzyloxy or pyridyl;

(ii) pyridyl, pyrimidyl or pyridazinyl, which is unsubstituted or substituted by a halogen atom;

(iii) furyl, thienyl, imidazolyl, thiazolyl, isothiazolyl, oxazolyl, isoxazolyl, thiadiazolyl, each of which is unsubstituted or substituted by (1-4C)alkyl or amino;

(iv) naphthyl, benzofuryl, benzothienyl, quinolyl or isoquinolyl;
(v) (3-6C)cycloalkyl;
(vi) piperidinyl or tetrahydropyranyl; or
(vii) (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl, pyridyl, (3-6C)cycloalkyl, oxa(4-6C)cycloalkyl, or aza(4-6C)cycloalkyl (which may bear an N-(1-4C)alkyl substituent); and $R^2$ is selected from

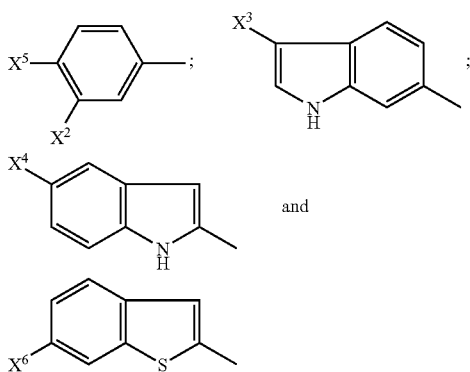

in which
$X^2$ represents a hydrogen atom, a halogen atom or an amino group;
$X^3$ represents a hydrogen atom, a methyl group, a chlorine atom or a bromine atom;
$X^4$ represents a hydrogen atom, a methyl group or a halogen atom;
$X^5$ represents a chlorine atom, a methoxy group or a methyl group; and
$X^6$ represents a hydrogen atom, a halogen atom or a methyl group;
or a pharmaceutically acceptable salt thereof.

2. A compound as claimed in claim 1, in which $R^1$ represents (1-4C)alkyl, which is unsubstituted or substituted by hydroxy, (1-4C)alkoxy, phenoxy, carboxy, aminocarbonyl, aminosulfonyl, (1-4C)alkylthio, phenylthio, pyridylthio, amino, (1-4C)alkylamino, di(1-4C)alkylamino, piperidin-1-yl, morpholino, trifluoromethyl, phenyl, imidazolyl pyridyl, (3-6C)cycloalkyl, oxa(4-6C)cycloalkyl, or aza (4-6C)cycloalkyl (which may bear an N-(1-4C)alkyl substituent).

3. A compound as claimed in claim 1, in which $R^3$ is 2-trifluoromethylpyrid-4-yl, 2-cyanopyrid-4-yl, pyrimidin-4-yl, 2-methoxypyrimidin-4-yl, or pyridazin-3-yl.

4. A compound as claimed in claim 1, in which $R^1$ represents:—
(i) phenyl, 2,3-methylenedioxyphenyl, 2-chlorophenyl, 2-methylphenyl, 2-methoxyphenyl, 2-trifluoromethylphenyl, 2-difluoromethoxyphenyl, 4-carboxyphenyl or 4-aminocarbonylphenyl;
(ii) pyrid-2-yl or pyrid-4-yl;
(iii) fur-2-yl, fur-3-yl, thien-2-yl, thien-3-yl, imidazol-2-yl, thiazol-4-yl, 2-methylthiazol-4-yl or 2-aminothiazol-4-yl;
(iv) naphth-1-yl, naphth-2-yl, benzofuryl, benzothienyl, quinolin-4-yl or quinolin-8-yl;
(v) cyclopropyl, cyclobutyl, cyclopentyl or cyclohexyl;
(vi) piperidin-4-yl or tetrahydropyran-4-yl; or
(vii) methyl, ethyl, propyl, 2-propyl, butyl, 2-methylpropyl, hydroxymethyl, 1-hydroxyethyl, methoxymethyl, 1-methoxyethyl, methylthiomethyl, 2-methylthioethyl, prop-2-ylthiomethyl, N,N-dimethylaminomethyl, phenylthiomethyl, pyrid-2-ylthiomethyl, carboxymethyl, 2-carboxyethyl, aminocarbonylmethyl, 2-aminocarbonylethyl, morpholinomethyl, 2,2,2-trifluoroethyl, benzyl, pyrid-2-ylmethyl, pyrid-3-ylmethyl, pyrid-4-ylmethyl, imidazol-1-ylmethyl, imidazol-4-ylmethyl, 3-methylimidazol-4-ylmethyl, cyclohexyl-4-ylmethyl, tetrahydropyran-4-ylmethyl, piperidin-1-ylmethyl or 1-methylpiperidin-4-ylmethyl.

5. A compound as claimed in claim 4, in which $R^1$ represents phenyl, 2-chlorophenyl, 2-methoxyphenyl, 2-trifluoromethylphenyl or 2-difluoromethoxyphenyl.

6. A compound as claimed in any one of claims 1, 2, 3, or 4, in which $X^2$ represents a hydrogen atom or a halogen atom.

7. A compound as claimed in claim 6, in which
$X^2$ represents a hydrogen atom or a fluorine atom;
$X^3$ represents a hydrogen atom a chlorine atom or a methyl group;
$X^4$ represents a chlorine atom;
$X^5$ represents a chlorine atom or a methoxy group; and
$X^6$ represents a chlorine atom.

8. A compound as claimed in claim 7, in which $R^2$ is 4-chlorophenyl, 4-methoxyphenyl, indol-6-yl, 3-methylindol-6-yl, 3-chloroindol-6-yl, 5-chloroindol-2-yl, or 6-chlorobenzo[b]thiophen-2-yl.

9. A compound as claimed in claim 8, in which $R^2$ is 4-methoxyphenyl, indol-6-yl or 5-chloroindol-2-yl.

10. A pharmaceutical composition, which comprises a compound as claimed in claim 1, together with a pharmaceutically acceptable diluent or carrier.

11. A process for preparing a compound as claimed in claim 1, which comprises
(a) reacting a compound of formula (II)

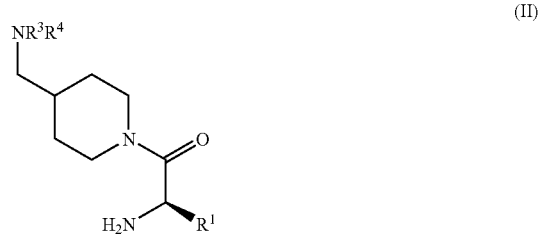

or a salt thereof, with a compound of formula (III)

or a reactive derivative thereof;

(b) reacting a compound of formula (IV)

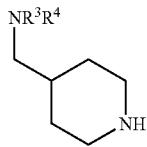

or a salt thereof, with a compound of formula (V)

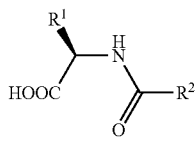

or a reactive derivative thereof; or (c) deprotecting a compound of formula

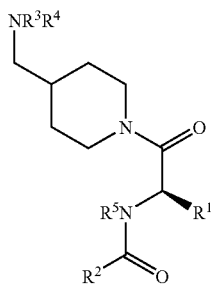

in which $R^5$ represents an amino protecting group;
followed, if a pharmaceutically acceptable salt is desired by forming a pharmaceutically acceptable salt.

12. A compound of formula (II)

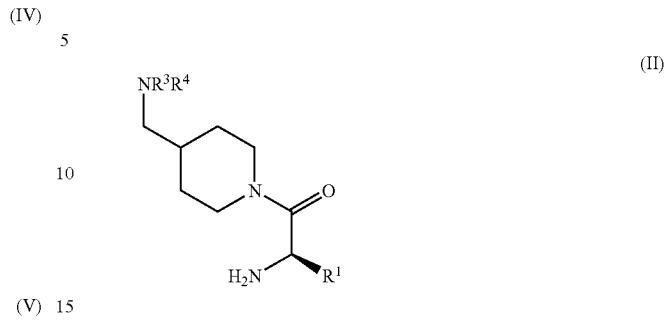

or a salt thereof, in which $R^1$, $R^3$ and $R^4$ are as defined in any one of claims 1, 2 and 3 to 5.

13. A compound of formula (VI)

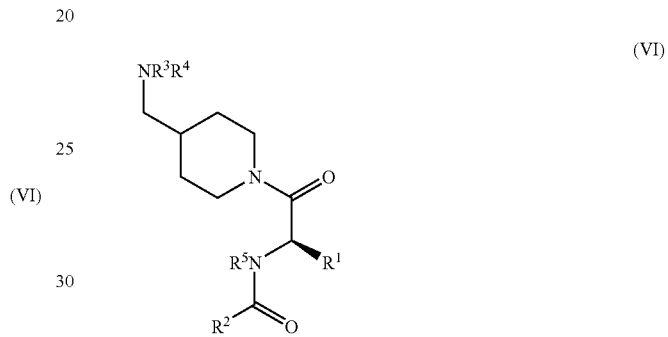

in which $R^5$ represents an amino protecting group, and $R^1$, $R^2$, $R^3$ and $R^4$ are as defined in claim 1, or a salt thereof.

14. A method of treating a thrombotic disorder in a subject requiring treatment, which comprises administering an effective amount of a compound as claimed in claim 1.

* * * * *